(12) United States Patent
Heggendorn et al.

(10) Patent No.: US 8,357,202 B2
(45) Date of Patent: Jan. 22, 2013

(54) J-CURVE FOR A FEMORAL PROSTHESIS COMPONENT

(75) Inventors: Marco A. H. Heggendorn, Pura (CH); Roger Scherrer, Schaffhausen (CH); Matthias Schäpper, Winterthur (CH)

(73) Assignee: Zimmer, GmbH, Winterthur (CH)

( * ) Notice: Subject to any disclaimer, the term of this patent is extended or adjusted under 35 U.S.C. 154(b) by 53 days.

(21) Appl. No.: 12/644,698

(22) Filed: Dec. 22, 2009

(65) Prior Publication Data

US 2011/0153026 A1 Jun. 23, 2011

(51) Int. Cl.
*A61F 2/38* (2006.01)
(52) U.S. Cl. .................. 623/20.14; 623/20.35
(58) Field of Classification Search ............... 623/20.14, 623/20.31, 20.35; A61F 2/38
See application file for complete search history.

(56) References Cited

U.S. PATENT DOCUMENTS

| | | |
|---|---|---|
| 3,798,679 A | 3/1974 | Ewald |
| 3,869,731 A | 3/1975 | Waugh et al. |
| 4,224,696 A | 9/1980 | Murray et al. |
| 4,224,697 A | 9/1980 | Murray et al. |
| 5,871,546 A | 2/1999 | Colleran et al. |
| 6,039,764 A | 3/2000 | Pottenger et al. |
| 6,165,221 A | 12/2000 | Schmotzer |
| 6,893,467 B1 | 5/2005 | Bercovy |
| 7,081,137 B1 | 7/2006 | Servidio |
| 7,351,263 B2 | 4/2008 | Afriat |
| 7,364,590 B2 | 4/2008 | Siebel |
| 7,544,210 B2 | 6/2009 | Schaefer et al. |
| 2007/0135926 A1 | 6/2007 | Walker |
| 2007/0260323 A1 | 11/2007 | Earl et al. |
| 2008/0058947 A1 | 3/2008 | Earl et al. |
| 2008/0097615 A1 | 4/2008 | Lipman et al. |
| 2010/0016979 A1* | 1/2010 | Wyss et al. .................. 623/20.27 |
| 2010/0036500 A1* | 2/2010 | Heldreth et al. ........... 623/20.31 |
| 2011/0125278 A1* | 5/2011 | Bercovy et al. ............ 623/20.21 |

OTHER PUBLICATIONS

U.S. Appl. No. 12/974,018, filed Dec. 21, 2010.

* cited by examiner

*Primary Examiner* — Thomas J Sweet
*Assistant Examiner* — Jason-Dennis Stewart
(74) *Attorney, Agent, or Firm* — Schwegman, Lundberg & Woessner, P.A.

(57) ABSTRACT

One or both of the condyles in a femoral component for a partial or total knee prosthesis includes a J-curve with a plurality of distinct radii, such as 5 or more radii. The centers of the radii are arranged along an arcuate path extending anteroposteriorly so that successively larger radii are serially arranged along the arcuate path from the posterior side of the femoral component to the anterior side. The femoral component provides a high degree of stability throughout the range of motion of the knee prosthesis, and facilitates a close approximation to the motion of a natural knee.

23 Claims, 1 Drawing Sheet

J-CURVE FOR A FEMORAL PROSTHESIS COMPONENT

BACKGROUND

1. Field of the Invention

The present disclosure relates generally to joint replacement surgery, and more particularly to femoral components used in total knee arthroplasty (TKA), in which the femoral components have a modified articular surface.

2. Brief Description of the Related Art

Joint replacement surgery is used to replace worn or damaged articular joint surfaces, thereby allowing the joint to function normally when it would otherwise not be possible to do so. Typically, an artificial joint includes metallic, ceramic and/or polymer components that are fixed to existing bone, which may or may not be resected prior to component affixation. In the case of total knee arthroplasty, a diseased and/or damaged natural knee joint is replaced with a prosthetic knee joint. Knee prostheses typically include a femoral component, a patellar component, a tibial tray or plateau and a tibial bearing insert coupled to the tibial tray. The femoral component generally includes a pair of laterally spaced condylar portions adapted to function similarly to the natural femoral condyles they replace, with articular distal surfaces of the condylar portions interacting with complimentary surfaces formed in a tibial bearing insert.

A goal of total knee arthroplasty procedures is to restore or enhance function of the natural knee while retaining as much of the knee's normal range of motion as possible. A natural knee may have a range of motion from 0° (full extension) to 135° (full flexion), for example. However, a reduced range of motion is sometimes experienced with some known knee prostheses and associated TKA procedures, resulting, for example, in a post operative range of motion of approximately 0-110°. Substantial efforts have been focused on providing "high flex" knee prostheses that offer a range of motion that is as close as possible to the natural knee.

In addition to range of motion considerations, mechanical functioning and longevity are also goals of knee prosthesis design. For example, minimization of joint stiffness and maximization of joint stability throughout the range of motion are desirable in total knee prostheses. Post-operative joint stability is a function of several factors, including surgical technique and implant design. Design efforts have been focused on promotion of prosthesis stability throughout the range of motion, and in particular at the "mid flexion" range of motion, which includes the range of motion around a knee flexion of about 45°.

One known design uses a single radius in the "J-curve" of the knee component condylar portions. The J-curve is the curve of the articular surface of the condylar portions as viewed in a sagittal plane that is medially or laterally offset to intersect with the articular surfaces of each condylar portion. In the "single radius" design, the center of the radius corresponds to the epicondylar axis, which is an axis approximately corresponding with the axis passing through the femoral attachments of the collateral ligaments of the knee. A single radius design typically corresponds to a range of motion from 10° (less than full extension) to 110° (less than full flexion). Thus, a "single radius" design, which seeks enhanced mid flexion stability, does not result in a full range of motion comparable to a natural knee.

Other known femoral components includes J-curves having three or four tangential radii with centers spaced apart from one another, such as shown in FIG. 3. In these designs, the rotational centers of the femur during flexion correspond to the arc centers of the J-curve of the femoral component. Because these radii each have different sizes, the rotational center displaces sharply in the range of flexion corresponding with a transition from one radius to the next, or neighboring, radius. This sharp and large displacement is believed to detract from knee prosthesis stability in these ranges of flexion.

What is needed is a new total knee prosthesis with a high degree of stability throughout a wide range of motion.

SUMMARY

The present disclosure provides a femoral component for a partial or total knee prosthesis in which one or both of the condyles of the femoral component include a J-curve with a plurality of distinct radii, such as 5 or more radii. The centers of the radii are arranged along an arcuate path extending anteroposteriorly so that successively larger radii are serially arranged along the arcuate path from the posterior side of the femoral component to the anterior side. The femoral component provides a high degree of stability throughout the range of motion of the knee prosthesis, and facilitates a close approximation to the motion of a natural knee.

In one embodiment, a femoral condylar implant has at least one condyle with an articular surface, in which the articular surface includes a J-shaped curve extending along the articular surface from a posterior side of the implant to an anterior side of the implant in a sagittal plane. The J-shaped curve has at least five radii that progressively increase in size from the posterior side to the anterior side, with respective centers of the radii tracing an arcuate path in which a center of a first radius is posterior of a center of a neighboring second radius when the first radius is smaller than the second radius.

In one aspect, the distance between any pair of neighboring radius centers may be between 1 mm and 25 mm. The distance between any pair of neighboring radius centers may also be between 1.5 mm and 15 mm, or between 3 mm and 9 mm, for example.

In another aspect, a ratio of a relatively smaller radius to a relatively larger radius in any pair of neighboring radii may be between 0.50 and 0.95.

In another aspect, the condylar implant may also include a mediolateral curve on a coronal plane. The J-shaped curve and the mediolateral curve cooperate to define the articular surface of the at least one condyle.

In another aspect, the condylar implant may also include a second condyle with a second J-shaped curve extending from a posterior side of the implant to an anterior side of the implant in a sagittal plane. The second J-shaped curve may have at least five radii that progressively increase in size from the posterior side to the anterior side so that respective centers of the radii trace an arcuate path in which a center of a first radius is posterior of a center of a neighboring second radius when the first radius is smaller than the second radius.

In another aspect, the J-shaped curve of the first condyle may be asymmetrical with the J-shaped curve of the second condyle. The J-shaped curve of the first condyle may also be symmetrical with the J-shaped curve of the second condyle, and may be a mirror image of the J-shaped curve of the second condyle.

In yet another aspect, the J-shaped curve defines at least six radii. The J-shaped curve may also define at least seven radii.

In still another aspect, an angle between a largest radius and a smallest radius of the at least five radii defines an angle of at least 130 degrees.

In another embodiment, a knee prosthesis includes a femoral component having a proximal surface sized to engage the distal end of a femur and an articular surface comprising a medial condyle and a lateral condyle. The articular surface includes at least one J-shaped curve extending from a posterior side of the implant to an anterior side of the implant in at least one sagittal plane, the plane intersecting at least one of the medial condyle and the lateral condyle. The J-shaped curve defines a plurality of radii progressively increasing in size from the posterior side to the anterior side, so that respective centers of the radii trace an arcuate path in which a center of a relatively smaller radius is posterior of the next larger radius. The distance between any pair of neighboring radius centers is less than 25 mm. Alternatively, the distance between any pair of neighboring radius centers may be less than 15 mm or less than 9 mm, for example.

In one aspect, a ratio of a relatively smaller radius to a relatively larger radius in any pair of neighboring radii may be between 0.50 and 0.95.

In another aspect, the knee prosthesis may include a mediolateral curve on a coronal plane. The J-shaped curve and the mediolateral curve may cooperate to define an articular surface of one of the medial condyle and the lateral condyle.

In another aspect, both of the medial condyle and the lateral condyle include the J-shaped curve, and the J-shaped curve of the medial condyle may be asymmetrical with the J-shaped curve of the lateral condyle. Alternatively, the J-shaped curve of the medial condyle may be symmetrical with the J-shaped curve of the lateral condyle, or may be a mirror image of the J-shaped curve of the lateral condyle.

In another aspect, an angle between a largest radius and a smallest radius of the at least five radii may define an angle of at least 130 degrees.

BRIEF DESCRIPTION OF THE DRAWINGS

The above-mentioned and other features and advantages of this disclosure, and the manner of attaining them, will become more apparent and the invention itself will be better understood by reference to the following description of an embodiment of the invention taken in conjunction with the accompanying drawings, wherein.

The exemplifications set out herein illustrate an exemplary embodiment of the present invention, and such exemplification is not to be construed as limiting the scope of the invention in any manner.

DETAILED DESCRIPTION

Figure 1:
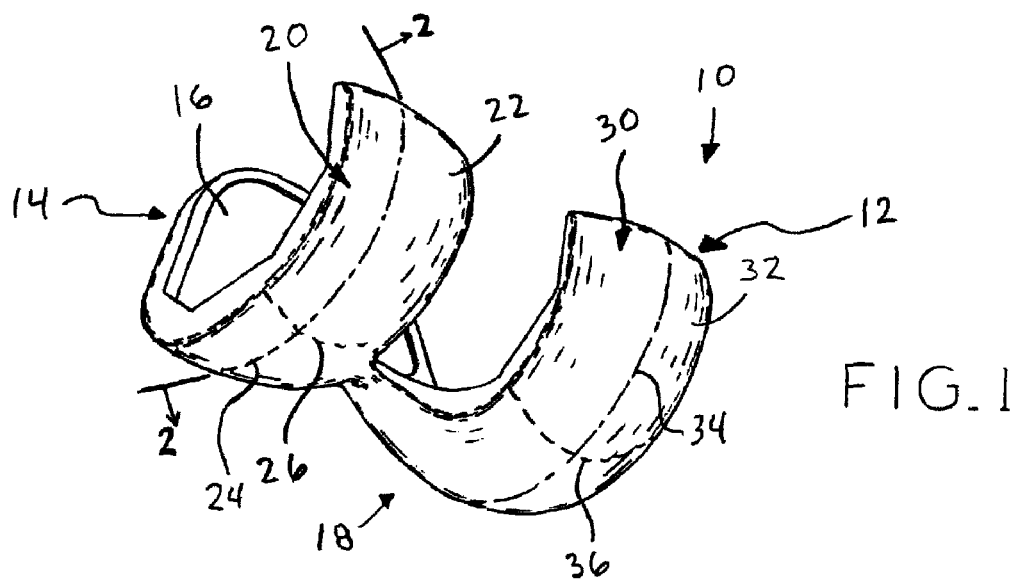
FIG. 1 is a perspective view of a femoral component of a total knee prosthesis in accordance with the present disclosure.

Referring to FIG. 1, femoral component 10 has posterior side 12 and anterior side 14 with a generally U-shaped profile extending therebetween. Proximal surface 16 is adapted to be secured to the distal end of a femur. The femur may or may not be resected prior to such attachment. A distal or articular surface 18 is disposed opposite the proximal surface 16 and is adapted to cooperate with a proximal surface of a tibial bearing member (not shown). Femoral component 10 may also be used in conjunction with natural tibial structures in a partial knee arthroplasty, or, alternatively, may be used in a total knee arthroplasty procedure as part of a total knee replacement (TKR). The TKR may include, for example, a tibial component with a distal end mounted to a proximal end of a tibia, femoral component 10 mounted to a distal end of a femur, and a tibial bearing member with a distal surface configured to engage the proximal end of the tibial component and a proximal surface sized and configured to cooperate with distal surface 18 of femoral component 10.

Referring still to FIG. 1, femoral component 10 includes first condyle 20 and second condyle 30. Condyles 20, 30 may be mirror images of one another reflected about a generally central sagittal plane, or may be substantially identical. Condyles 20, 30 may also be asymmetrical, such as with one condyle larger than the other. First condyle 20 has first articular surface 22 comprising first J-curve 24 and first mediolateral curve 26. J-curve 24 is defined in a sagittal plane intersecting first condyle 20, while mediolateral curve 26 "follows" J-curve 24 through a plurality of coronal planes oriented generally perpendicularly to the sagittal plane. Moreover, first articular surface 22 may be defined or "built" by sweeping mediolateral curve 26 along J-curve 24 to produce a generally convex three dimensional profile of first articular surface 22 which corresponds with the shape of a natural femoral condyle. Mediolateral curve 26 may have a curvature that varies over the extent of J-curve 24, such as by having a generally larger radius at anterior side 16 as compared with posterior side 12. However, mediolateral curve 26 may also have other geometrical arrangements.

Similarly, second condyle 30 has second articular surface 32 comprising second J-curve 34 and second mediolateral curve 36. As also noted above, second condyle 30 and first condyle 20 may or may not mirror or replicate one another. Thus, second articular surface 32 may or may not mirror or replicate first articular surface 22 and second mediolateral curve 36 may or may not have a geometry varying from first mediolateral curve 26. However, in an exemplary embodiment, first J-curve 24 and second J-curve 34 will each comprise multiple radii with centers tracing an arcuate path, in accordance with the present disclosure and described below. Further, the distance between first and second J-curves 24, 34, or "bearing spacing," generally varies in the range of 30 mm to 50 mm, depending on circumstances such as prosthesis geometry and the overall size of the prosthesis.

Figure 2:
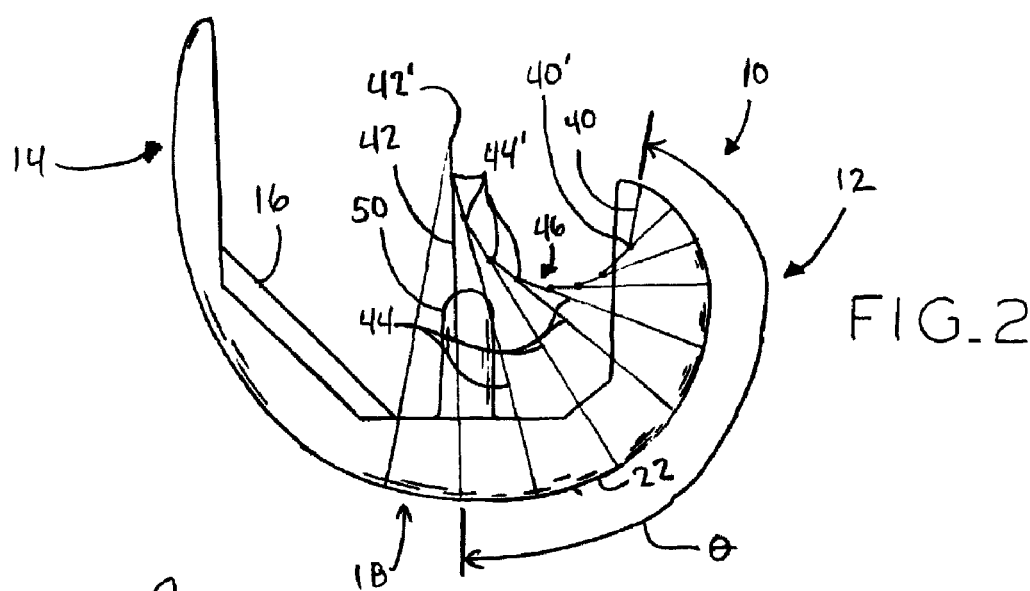
FIG. 2 is an elevation view of the femoral component shown in FIG. 1, illustrating multiple radii thereof.
Figure 3:
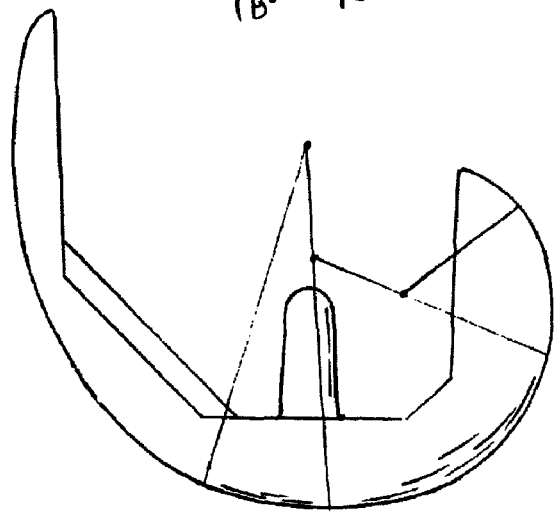
FIG. 3 is an elevation view of a known femoral component used in total knee arthroplasty.

Referring now to FIG. 2, first J-curve 24 on first articular surface 22 is shown. J-curve 24 includes posterior radius 40 which is relatively small, resulting in a tight radius of curvature at posterior side 12 of articular surface 22. J-curve 24 also includes anterior radius 42 disposed toward anterior side 14 of articular surface 22 and terminating at distal surface 18. Anterior radius 42 is relatively large, resulting in a large radius of curvature at the portion of first articular surface 22 corresponding with the terminus of anterior radius 42. Between anterior radius 42 and posterior radius 40 are a plurality of intermediate radii 44, such as three or more intermediate radii. The intermediate radius 44 disposed anterior of posterior radius 40 is larger than posterior radius 40, and successive ones of intermediate radii 44 are larger than the next or neighboring radius along the posterior direction. Thus, radii 40, 44, 46 grow successively and serially larger from the posterior side 12 toward the anterior side 14.

Posterior radius 40 defines a posterior radius center 40' generally disposed near posterior side 12. Anterior radius 42 defines anterior radius center 42' disposed anteriorly of posterior center 40' and generally toward anterior side 14. Intermediate radii define respective intermediate radius centers 44', and are generally disposed between posterior center 40' and anterior center 42'. Any given intermediate radius center 44' is disposed between two neighboring radius centers, with the neighboring radius center in the posterior direction belonging to the next smaller radius, and the neighboring radius on the anterior side belonging to the next larger radius. Thus, radius centers 40', 42', 44' are successively or serially arranged anteroposteriorly so that the centers of successively larger radii are serially ordered from posterior side 12 toward anterior side 14. That is to say, radii are arranged smallest-to-largest from the smallest radius and radius center (i.e., posterior radius 40 and center 40') to the largest radius and radius center (i.e., anterior radius 42 and center 42').

Referring still to FIG. 2, radius centers 40', 42', 44' trace arcuate path 46. More particularly, each radius center is disposed along the extent of the neighboring radius, and is spaced from the neighboring radius center. However, it is contemplated that respective radius centers may be spaced away from the extent of the neighboring radius. Because J-curve 24 includes a plurality of radii, such as at least five radii, the distance D between neighboring radius centers along arcuate path 46 is minimal. Advantageously, as femoral component 10 articulates with another surface (such as a tibial bearing member or the surface of a natural tibia) through a range of motion, the displacement of the center of rotation defined by articular surface 22 is relatively small when transitioning from one radius of curvature to a neighboring radius, thereby maximizing prosthesis stability in the range of motion corresponding with radius transition points. For example, in an exemplary embodiment, the distance D between any pair of neighboring radius centers may be as little as 1 mm, 1.5 mm or 3 mm and as great as 9 mm, 15 mm or 25 mm, or within any range defined by any of the foregoing values.

In further exemplary embodiments, differently sized femoral components having a J-curve in accordance with the present disclosure may be used to replace natural femoral structures of correspondingly differing sizes. For example, a relatively small size femoral component may have a distance D between any pair of neighboring radius centers in the range of 1 mm to 9 mm. A medium size femoral component may have a distance D between any pair of neighboring radius centers in the range of 1.5 mm to 15 mm. A relatively large size femoral component may have a distance D between any pair of neighboring radius centers in the range of 3 mm to 25 mm.

Another metric useful to describing a J-curve in accordance with the present disclosure is the ratio of the lengths of any two neighboring radii. One factor in this ratio, as discussed above, is that the displacement from one radius center to a neighboring radius center is relatively small. Another factor stems from the J-curve following an arcuate path. Accounting for these two factors, the ratio of one radius to a neighboring, larger radius in a J-curve according to the present disclosure is between 0.50 and 0.95. This range of ratios applies for the various pairs of radii within a J-curve in accordance with the present disclosure. The ratio also applies to a variety of different sizes and configurations for femoral components incorporating a J-curve in accordance with the present disclosure.

Advantageously, a femoral component incorporating a J-curve in accordance with the present disclosure offers a high degree of stability through a wide range of flexion. Referring to FIG. 2, the range of motion along articular surface 22 is represented by θ, which is the angle between posterior radius 40 and anterior radius 42. The multiple radii of the present disclosure can be distributed over any desired angular range, such as over the full range of motion of a natural knee (i.e., from)0°-135°, while also maintaining a high degree of stability by minimizing the distance between pairs of neighboring radius centers, as described above.

Also advantageously, a femoral component including a J-curve in accordance with the present disclosure may be used with a wide variety of knee joint prostheses, including in revision surgeries for existing or previously implanted knee joint prostheses.

Femoral component 10 may include peg 50 (FIG. 2) which may aid in attachment of femoral component 10 to the distal end of a femur. Femoral component 10 may also be useable with systems including spines for guided motion, such as systems in which a spine is integrally formed with a tibial component or in which a spine is formed as a separate part of a knee prosthesis. Moreover, because an articular surface including a J-curve in accordance with the present disclosure may be formed on any femoral component, the high stability and wide range of motion permitted by the J-curve may be combined with other knee prosthesis technologies, such as mobile bearing designs, rotatable and/or translatable spine designs, and the like.

While this invention has been described as having an exemplary design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A femoral condylar implant having at least one condyle with an articular surface, the articular surface adapted for use with a knee and comprising:
    a J-shaped curve extending along the entire articular surface from a posterior side of the implant to an anterior side of the implant in a sagittal plane, said posterior side positioned to contact the articular surface at greater than 90 degrees flexion of the knee, said anterior side positioned to contact the articular surface at full extension of the knee,
    said J-shaped curve defining at least five radii that progressively, serially increase in size along the entire articular surface from said posterior side to said anterior side, respective centers of said radii tracing an arcuate path in which a center of a first radius is posterior of a center of a neighboring second radius when said first radius is smaller than said second radius, such that the largest of said five radii defines an angle with the smallest of said five radii that is greater than 90 degrees, and wherein there are no radii having a decreasing size along the entire articular surface from said posterior side to said anterior side.

2. The knee prosthesis of claim 1, wherein a distance between any pair of neighboring radius centers is between 1 mm and 25 mm.

3. The knee prosthesis of claim 1, wherein a distance between any pair of neighboring radius centers is between 1.5 mm and 15 mm.

4. The knee prosthesis of claim 1, wherein a distance between any pair of neighboring radius centers is between 3 mm and 9 mm.

5. The femoral condylar implant of claim 1, wherein a ratio of a relatively smaller radius to a relatively larger radius in any pair of neighboring radii is between 0.50 and 0.95.

6. The femoral condylar implant of claim 1, further comprising a mediolateral curve on a coronal plane, wherein said J-shaped curve and said mediolateral curve cooperate to define the articular surface of said at least one condyle.

7. The femoral condylar implant of claim 1, comprising a second condyle with a second J-shaped curve extending from said posterior side of the implant to said anterior side of the implant in a second sagittal plane, said second J-shaped curve defining at least five radii that progressively increase in size from said posterior side to said anterior side, respective centers of said radii of said second J-shaped curve tracing an arcuate path in which a center of a first radius of said second J-shaped curve is posterior of a center of a neighboring second radius of said second J-shaped curve when said first radius is smaller than said second radius.

8. The femoral condylar implant of claim 7, wherein said J-shaped curve of said first condyle is asymmetrical to said J-shaped curve of said second condyle.

9. The femoral condylar implant of claim 7, wherein said J-shaped curve of said first condyle is symmetrical to said J-shaped curve of said second condyle.

10. The femoral condylar implant of claim 9, wherein said J-shaped curve of said first condyle is a mirror image of said J-shaped curve of said second condyle.

11. The femoral condylar implant of claim 1, wherein said J-shaped curve defines at least six radii.

12. The femoral condylar implant of claim 1, wherein said J-shaped curve defines at least seven radii.

13. The femoral condylar implant of claim 1, wherein said angle defined between the largest of said at least five radii and the smallest of said at least five radii is at least 100 degrees.

14. The femoral condylar implant of claim 1, wherein said angle defined between the largest of said at least five radii and the smallest of said five radii is up to 130 degrees, whereby the progressive increase in size of said at least five radii continues into deep flexion.

15. A knee prosthesis comprising a femoral component having a proximal surface sized to engage the distal end of a femur and an articular surface comprising a medial condyle and a lateral condyle each shaped to articulate with a tibial articular surface through a range of motion from extension to flexion, said articular surface comprising:
at least one J-shaped curve extending along the entire articular surface from a posterior side of the implant to an anterior side of the implant in at least one sagittal plane, said posterior side positioned to contact the tibial articular surface at up to 130 degree flexion, said anterior side positioned to contact the articular surface at full extension, said sagittal plane intersecting at least one of said medial condyle and said lateral condyle,
said J-shaped curve defining a plurality of radii progressively, serially increasing in size along the entire articular surface from said posterior side to said anterior side such that the largest of said plurality of radii defines an angle with the smallest of said plurality of radii that is at least 130 degrees,
respective centers of said radii tracing an arcuate path in which a center of a relatively smaller radius is posterior of a center of a larger radius, and a distance between any pair of neighboring radius centers is less than 25 mm, and wherein there are no radii having a decreasing size along the entire articular surface from the posterior side to the anterior side.

16. The knee prosthesis of claim 15, wherein said distance between any pair of neighboring radius centers is less than 15 mm.

17. The knee prosthesis of claim 15, wherein said distance between any pair of neighboring radius centers is less than 9 mm.

18. The femoral condylar implant of claim 15, wherein a ratio of a relatively smaller radius to a relatively larger radius in any pair of neighboring radii is between 0.50 and 0.95.

19. The femoral condylar implant of claim 15, further comprising a mediolateral curve on a coronal plane, wherein said J-shaped curve and said mediolateral curve cooperate to define the articular surface of at least one of said medial condyle and said lateral condyle.

20. The femoral condylar implant of claim 15, wherein both of said medial condyle and said lateral condyle comprise said J-shaped curve, and said J-shaped curve of said medial condyle is asymmetrical with said J-shaped curve of said lateral condyle.

21. The femoral condylar implant of claim 15, wherein both of said medial condyle and said lateral condyle comprise said J-shaped curve, and said J-shaped curve of said medial condyle is symmetrical with said J-shaped curve of said lateral condyle.

22. The femoral condylar implant of claim 21, wherein said J-shaped curve of said medial condyle is a mirror image of said J-shaped curve of said lateral condyle.

23. A femoral condylar implant adapted to be implanted in a knee, the implant comprising:
at least one condyle defining a femoral articular surface, said femoral articular surface shaped to articulate with a tibial articular surface through the range of motion of the knee; and
a J-shaped curve extending along the entire femoral articular surface from a posterior side of the femoral articular surface to an anterior side of the femoral articular surface in a sagittal plane,
said J-shaped curve defined by at least five radii spanning the entire range of motion of the knee, said at least five radii progressively, serially increase in size along the entire articular surface from said posterior side to said anterior side of said femoral articular surface, respective centers of said radii tracing an arcuate path in which a center of a first radius is posterior of a center of a neighboring second radius when said first radius is smaller than said second radius, and wherein there are no radii having a decreasing size along the entire articular surface from the posterior side to the anterior side.

* * * * *

UNITED STATES PATENT AND TRADEMARK OFFICE
CERTIFICATE OF CORRECTION

PATENT NO. : 8,357,202 B2   Page 1 of 1
APPLICATION NO. : 12/644698
DATED : January 22, 2013
INVENTOR(S) : Heggendorn et al.

It is certified that error appears in the above-identified patent and that said Letters Patent is hereby corrected as shown below:

On the Title Page, Item (56), in column 2, under "Other Publications", line 1, delete "U.S. Appl. No. 12/974,018, filed Dec. 21, 2010." and insert --"U.S. Appl. No. 12/974,018, Preliminary Amendment filed Dec. 21, 2010", 4 pgs.--, therefor Signed and Sealed this
Eighteenth Day of November, 2014

Michelle K. Lee
*Deputy Director of the United States Patent and Trademark Office*